United States Patent [19]

Milam

[11] Patent Number: 5,551,845
[45] Date of Patent: Sep. 3, 1996

[54] MEDICAL AIR VACUUM

[76] Inventor: David N. Milam, 214 Chimney Hill, West Monroe, La. 71291

[21] Appl. No.: 370,687

[22] Filed: Jan. 10, 1995

[51] Int. Cl.⁶ .................................................. F04B 49/00
[52] U.S. Cl. ..................... 417/290; 417/298; 417/269; 417/313; 417/53; 137/205; 137/209; 55/259; 55/320; 433/92
[58] Field of Search .................................. 417/269, 290, 417/298, 313, 306, 446, 63, 53; 433/92; 137/205, 209; 55/257.6, 259, 320

[56] References Cited

U.S. PATENT DOCUMENTS

| | | | |
|---|---|---|---|
| 3,734,122 | 5/1973 | Cousins | 417/313 |
| 3,932,065 | 1/1976 | Ginsberg et al. . | |
| 4,022,593 | 5/1977 | Lerner | 55/259 |
| 4,160,323 | 7/1979 | Tracy . | |
| 4,359,085 | 11/1982 | Mueller . | |
| 4,588,359 | 5/1986 | Hikade | 417/298 |
| 4,957,491 | 9/1990 | Parker . | |
| 5,017,135 | 5/1991 | Meyer | 433/92 |
| 5,053,120 | 10/1991 | Mollmann | 210/86 |
| 5,205,743 | 4/1993 | Ludvigsson et al. | 433/92 |
| 5,211,558 | 5/1993 | Bailey et al. . | |
| 5,222,871 | 6/1993 | Meyer et al. . | |

OTHER PUBLICATIONS

DEN–TAL–EZ, INC., CustomVac™ Technical Sales Data Sheet, *Dynamic Dry Dual Vacuum System*, Nov. 1993.
Curtis-Toledo, Inc., *Challenge Air*, air compressor installation and operating instruction manual, Jul. 1993, pp. 14, 15 and 18, 19.
DEN–TAL–EZ, INC., CustomVac™ Technical Sales Data Sheet, *Dual Voltage Single Pump*, Apr. 1993.
The University of Texas, Health Science Center at San Antonio, *Comparison Testing of Dental Liquid Ring Vacuum Pumps*, Oct. 5, 1992.
GAST, *Separate Drive Rotary Vane*, date unknown, but believed to be prior art.
Fuji Electric Corp. of America, *Ring Compressors*, date unknown, but believed to be prior art.
Apollo Dental Products, Inc. *UltraVac . . . The Only One*, date unknown, but believed to be prior art.
Curtis–Toledo, *The Single State "Econo" Line Air Compressor*, date unknown, but believed to be prior art.

*Primary Examiner*—Charles Freay
*Attorney, Agent, or Firm*—Vaden, Eickenroht, & Thompson, L.L.P.

[57] ABSTRACT

An apparatus is provided for supplying vacuum and compressed air utilities for dental and medical applications. The apparatus comprises a reciprocating piston air compressor for simultaneously producing vacuum pressure at an intake valve thereof and compressed air at an exhaust valve thereof, the vacuum being used to draw air, water vapor, and effluent such as bodily fluids and tissue through a conduit. Effluent and water vapor are separated from the air stream and discharged into a drain. The desired vacuum is maintained by a regulator carried by the compressor. A receiver is also carried by the compressor for receiving and storing the compressed air from the compressor.

14 Claims, 4 Drawing Sheets

MEDICAL AIR VACUUM

BACKGROUND OF THE INVENTION

The present invention relates to systems that supply a partial vacuum and pressurized air primarily for medical and dental facilities. In a dentist's office, for example, a partial vacuum is used to remove saliva, tissue, rinse liquids, and tooth filling particles from a patient's mouth. Pressurized air is required for pneumatic dental tools such as high speed drills, and for clearing a localized area of a patient's mouth for examination or treatment.

The state of the art heretofore in this field is represented by the teachings of U.S. Pat. Nos. 3,734,122 and 5,222,871. In each of these patents, a partial vacuum is provided by a liquid ring vacuum pump and pressurized air is provided by one ('122) or two ('871) reciprocating piston compressors. Each pump and compressor is described as being provided with a corresponding electric motor, so the '122 apparatus requires two such motors and the '871 apparatus requires three.

A liquid ring vacuum pump utilizes a high speed impeller that swirls water in a housing to create a positive seal and to remove air from the housing creating a partial vacuum, hereinafter referred to only as a "vacuum." This type of pump requires a constant supply of water to generate a vacuum and to remove heat from the pump. A water supply and drain must therefore be readily available before installing a liquid ring system. Water use is of course an important environmental as well as economic factor in many areas. A typical liquid ring vacuum pump consumes 30 gallons of water per hour. Therefore, such a pump operating 40 hours per week will consume 60,000 gallons of water in a 50 week working year.

Even with a water recycling unit installed, liquid ring pumps require some 10,000 gallons of water annually. Furthermore, recycled water will inevitably pick up contaminants as the water is recirculated through a liquid ring pump, tending to make the water somewhat abrasive. The resulting "gray water" is known to reduce the life of the pump's seals and therefore increases the maintenance requirements and operating costs of a liquid ring pump.

The systems of the '122 and '871 patents further require multi-level frames for minimizing the footprint requirements of the numerous system components. The '122 patent discloses an upright two-level cabinet-type frame having a liquid ring vacuum pump mounted in the base thereof and a compressor mounted on a platform suspended from the top of the cabinet. The compressor drive motor is mounted to the underside of the platform and the pump drive motor is mounted in the base of the cabinet.

The '871 patent describes an upright three-level frame in which the two compressors and their respective motors are mounted on the upper-most level of the frame. A liquid ring pump and its drive motor are mounted on the middle level, and an air receiving tank is positioned on the lower level.

Access to the components of the systems described in these patent is restricted by placement of the components in upright frames. A technician must therefore reach through the frame, possibly while on a ladder, to obtain access to and service the system components. Furthermore, the placement of heavy components such as pumps, compressors, and their respective drive motors at intermediate or upper levels within the frame tends to make such a system top heavy and certainly unstable in any situation that requires transport or relocation of the frame.

In response to the hereinbefore described problems, it is an object of the present invention to provide vacuum and compressed air utilities in a dental or medical facility from a single "frameless" reciprocating piston device and electric motor. The reciprocating piston device's crankcase and cylinders provide attachment points for all necessary controls and related system accessories. This improvement reduces the number of required components, avoids the need for a multilevel frame or cabinet, and further reduces the corresponding floor space requirements for the system.

It is a further object of this invention to provide an apparatus that delivers high vacuum levels without using large amounts of water.

It is a further object of the present invention to provide an apparatus that supplies dry compressed air without the need for an air drier.

It is a still further object of the present invention to provide such apparatus with support for the motor driving the reciprocating piston device that automatically adjusts the tension in a drive belt between the motor and the device as the belt stretches.

It is a still further object of the present invention to provide such an apparatus that is reliable, easy to service, and economical to purchase and operate.

SUMMARY OF THE INVENTION

These and other objects and advantages are achieved, in accordance with the illustrated embodiments of the present invention, by an apparatus and method that comprise a reciprocating piston device for simultaneously drawing a vacuum in an intake line and delivering compressed air in an exhaust line thereof. The vacuum draws a stream of air, water vapor, and effluent such as bodily fluids and tissue through the intake line toward the reciprocating piston device. The effluent and water vapor are separated from the air stream upstream of the reciprocating piston device and then discharged through a drain. The desired vacuum is maintained by a regulator carried by the reciprocating piston device in the intake line. A receiver is further carried by the device to receive the compressed air delivered by the device.

In the preferred embodiment, the reciprocating piston device comprises a plurality of cylinders. The intake line is connected to two of the cylinders to provide the desired vacuum pressure, while the exhaust line is connected to a third cylinder to produce compressed air.

BRIEF DESCRIPTION OF THE DRAWINGS

In the drawings, wherein like reference characters are used throughout to describe like parts:

FIG. 3A is a plan view of the pivotal motor support platform of FIG. 3;

DETAILED DESCRIPTION OF THE PREFERRED EMBODIMENT

The preferred embodiment of the present invention, illustrated in FIGS. 1, 3, 4, and 5, comprises oil-lubricated reciprocating piston device 10 that simultaneously produces a vacuum and compressed air. The vacuum is used to draw a stream of air, water vapor, and effluent such as bodily fluids and tissue through intake port 3 in manifold plate MP and intake line or conduit toward reciprocating piston device 10.

Device 10 is a modified multi-cylinder, reciprocating piston Curtis-Toledo "Econo" line air compressor. The reciprocating piston device has three cylinders, each with a bore of 3.94 inches, a stroke of 2.75 inches, and an operating speed of 400–750 rpm. In operation, the reciprocating piston device produces a vacuum in its crankcase by way of the intake valves (not shown) of two of the device's cylinders. The intake or suction strokes of the two vacuum cylinders, which are manifolded together, are staggered to provide a continuous flow of air into the crankcase to maintain a substantially constant vacuum in conduit 82.

The intake valves of the two vacuum cylinders of reciprocating piston device 10 are spring-loaded in closed position and are designed to open when the pressure within the respective cylinders drops approximately one inch of mercury below the pressure in conduit 82 as the pistons are withdrawn within the respective cylinders.

Figure 3:
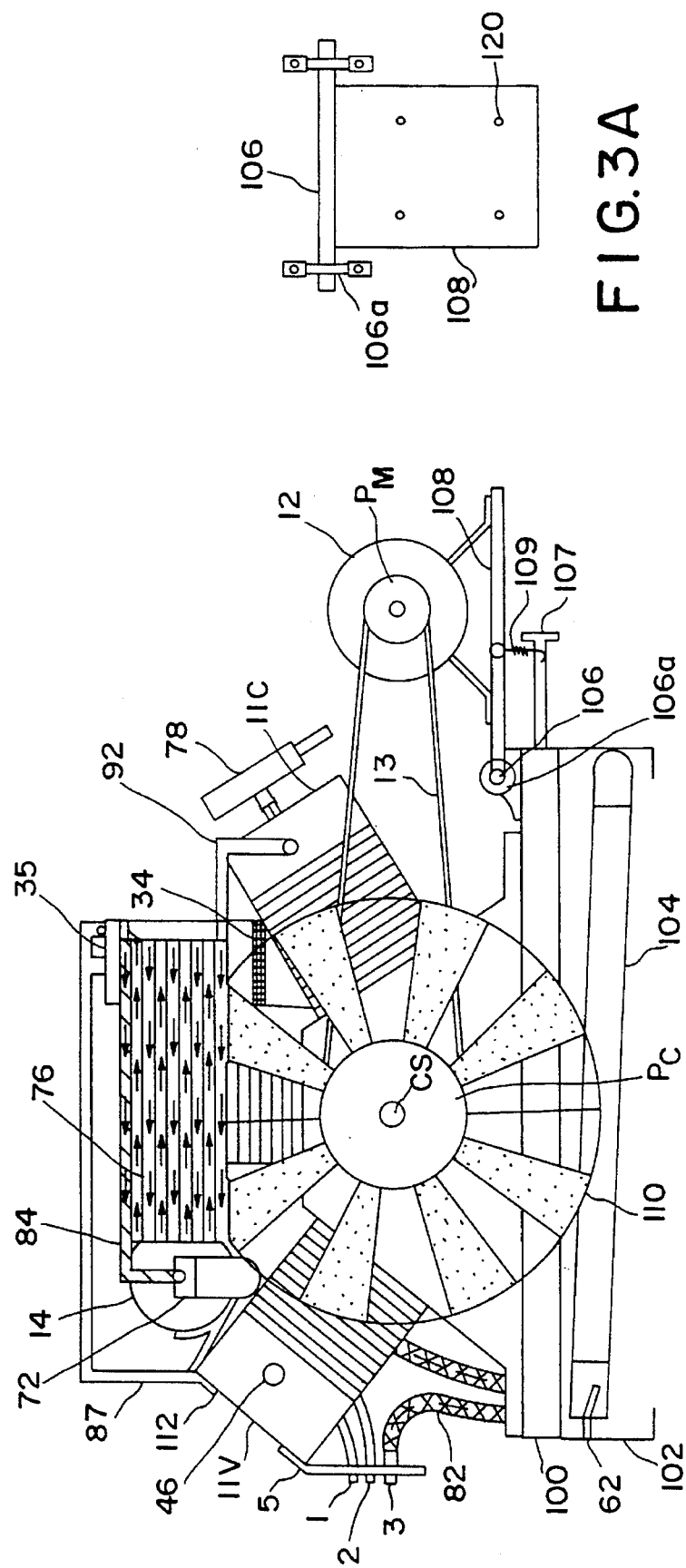
FIG. 3 is a front side view, partly in section and partly in elevation, of the embodiment of FIG. 1.
Figure 4:
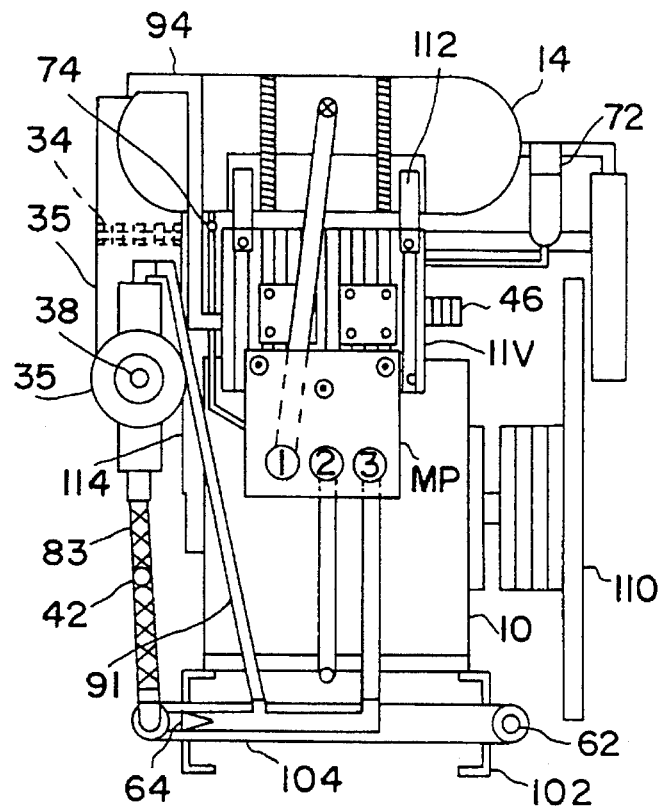
FIG. 4 is a rear view in elevation of the embodiment of FIG. 1.

Referring to FIGS. 3 and 3A, reciprocating piston device 10 is driven by electric motor 12 via motor pulley Pm, drive belt 13, and crankcase pulley Pc. Electric motor 12 is mounted on plate 108 by bolts (not shown) extending through holes (not shown) in motor support legs 122 and holes 120 in plate 108. The plate is connected at one end to shaft 106 that is mounted for rotation by bearing 106a. As a result, motor 12 is supported in a substantially horizontal position by drive belt 13. The combined weight of motor 12 and support plate 108 act to create a moment about shaft 106. This moment is born by drive belt 13, loading the drive belt in tension and automatically compensating for stretch therein. A spring tensioner 109 is attached between support plate 108 and baseplate extension 107 to reduce vibrational forces that would otherwise occur at shaft 106. Spring tensioner 109 further allows for easy removal and replacement of drive belt 13.

Cooling for reciprocating piston device 10 is provided by a large fan blade 110 that bolts directly to crankshaft CS. Forced convection cooling for reciprocating piston device 10 will therefore be provided as long as the device is operating, with no resulting discernable power consumption.

With reference again to FIG. 1, the intake valves of the two vacuum cylinders are connected by way of intake conduit 82 to vacuum intake port 3. The intake port is connected to the conduit system of the building in which the apparatus is utilized, and ultimately to a suction nozzle (not shown) for use in treating a patient. Upon start-up of reciprocating piston device 10, a vacuum is initiated pulling atmospheric air and system particles and fluids, i.e., effluent, through port 3 and into conduit 82 for effluent and water vapor separation. Full vacuum potential will typically be achieved in 20 to 45 seconds.

Figure 1:
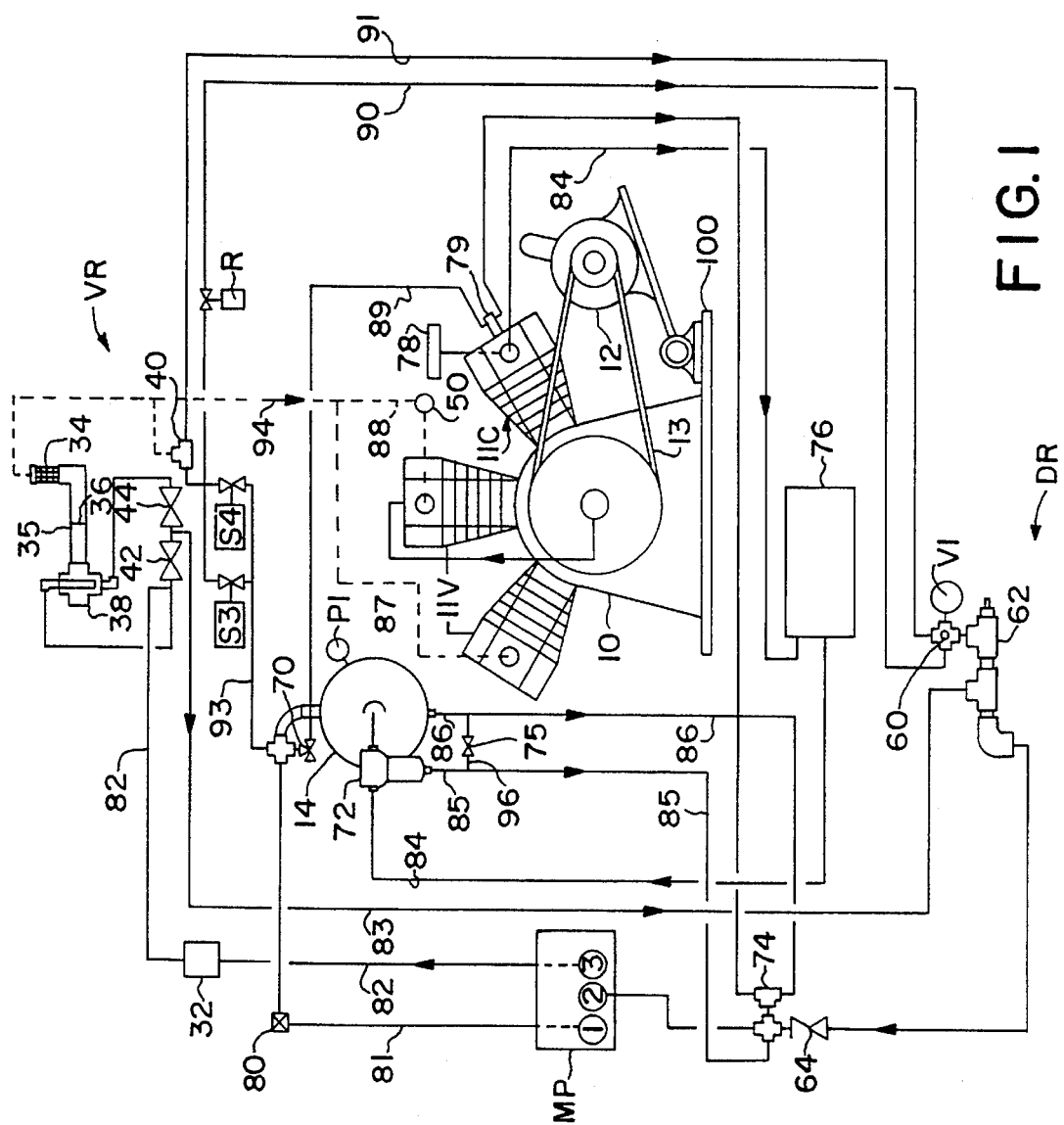
FIG. 1 is a flow diagram of the present invention.
Figure 5:
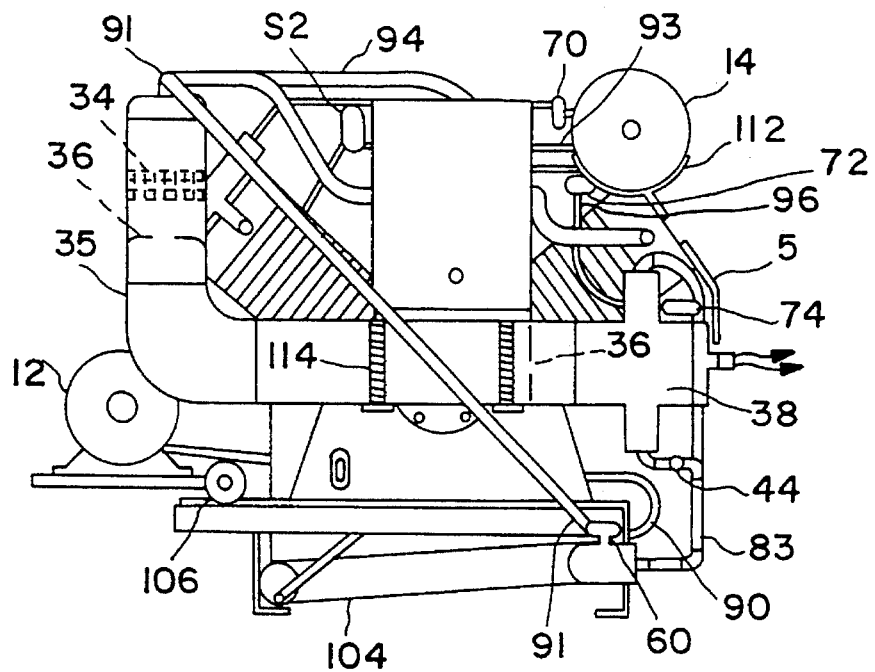
FIG. 5 is a side view in elevation of the embodiment of FIG. 1.

Means are carried by reciprocating piston device 10 in communication with conduit 82 for separating effluent and water vapor from the vacuum stream to avoid damage to the device. The separating means collectively makes up a subsystem of the apparatus that is referred to as the Vacuum Receiver (VR). In a particular embodiment, the VR comprises strainer 32, PVC assembly 35, float switch 38, demister 34, and vacuum equalization valve 40. Strainer 32 filters any solid particles such as bodily tissue that are drawn towards the VR via port 3 with the system air and fluids. Fluids in the stream are drawn by the reciprocating piston device's vacuum through strainer 32 and conduit 82 and enter 4" diameter PVC assembly 35. The PVC assembly, shown more particularly in FIG. 5, is attached at one end to high-level, shut down float switch 38 and contains at least one condensate baffle plate 36. Float switch 38 is normally closed, but opens when it senses a flooded condition in PVC assembly 35 of the VR to shut down the electrical circuit energizing reciprocating piston device 10, thereby preventing fluids from reaching the crankcase. Condensate baffle plate 36 and stainless steel wool pack demister 34 condense and collect water vapor entrained in the air stream drawn into the VR. PVC assembly 35 is sloped ten degrees towards float switch 38 to facilitate drainage of collected condensate through check valve 44 into conduit 83, as illustrated in FIG. 1.

Vacuum equalization valve 40 is normally opened and allows the vacuum pressure generated in the VR to be communicated through conduit 91 to the Drain Receiver (DR), discussed below. Thus, valve 40 provides for equal vacuum pressure in the VR and the DR. Since the VR is carried by the reciprocating piston device 10 at a height above the DR, condensate from the VR will migrate by gravitational force down through conduit 83 to the DR as long as both subsystems are at an equal pressure.

Means are also carried by reciprocating piston device 10 for regulating the pressure level of the vacuum in the VR. Preferably, the regulating means comprises a vacuum breaker 50 that regulates the vacuum pressure at intake port 3 to a level of 10–12 inches of mercury.

The present invention further comprises means communicating with the vacuum receiver separating means, or VR, for draining the effluent and humidity condensate separated from the vacuum stream. The draining means represents a subsystem, the Drain Receiver (DR), that comprises a conduit 91, check valve 64, and float switch 62.

Compressed air from receiver tank 14 (discussed further below) is used to activate a drain cycle in the DR. When the DR collects fluid in sufficient quantity to activate float switch 62, the float switch closes, signaling an off-delay timer (not shown) to electrically energize air solenoid valve S4. Solenoid valve S4 opens, delivering an air pressure signal from receiver tank 14 to the activation side of vacuum equalization valve 40 causing the normally open valve 40 to close. This severs the connection between the VR and the DR, canceling the vacuum pressure previously delivered from the VR to the DR.

The air solenoid charge from receiver tank 14 is regulated to 5 psi by regulator R and is conveyed to the DR via conduit 90. As the DR is pressurized to 5 psi, check valves 42 and 44 are sealed shut by the rising air pressure. Fluids in the DR, having nowhere else to go, are expelled through check valve 64, overcoming the valve's 1 psi spring pressure, and discharged out of waste discharge port 2. The link between the DR and VR is reestablished when the off-delay timer times out and solenoid valve S4 closes, opening vacuum equalization valve 40.

Air solenoid valve S3, normally closed, is automatically activated when the apparatus shuts down or loses power to initiate a purge cycle. An off-delay timer (not shown) electrically energizes valve S3 and the DR is purged of any remaining fluids until the off-delay timer times out. This feature minimizes stagnation of the condensate collected in the DR after the last receiver condensate drain cycle of the day.

The present invention further comprises means carried by the reciprocating piston device 10 for receiving the compressed air delivered from the device. Compressed air is provided by a single dedicated cylinder of reciprocating piston device 10, indicated as 11C in FIGS. 1 and 3. The remaining two cylinders of reciprocating piston device 10 will cooperate to provide continuous vacuum utilities, as described above, and are indicated as 11V. The air receiving means comprises an exhaust line or conduit 84, pilot valve 70, and receiver tank 14. The pressure within receiver tank 14 is controlled by pilot valve 70 mounted to the tank, to maintain a differential of 90 to 120 psi with the ambient air outside the tank.

Pilot valve 70 further controls the duration of air compression, by way of conduit 89 and intake valve unloader 79. Upon startup of the apparatus, valve unloader 79 permits the intake valve to operate normally for delivery of compressed air to air receiver tank 14. When the pressure in receiver tank 14 exceeds ambient air pressure by 120 psi, pilot valve 70 actuates unloader 79 to hold the intake valve of cylinder 11C open during both suction and discharge strokes. As a result, compressed air is no longer delivered to receiver tank 14.

As the compressed air in tank 14 is consumed, the pressure differential between receiver tank 14 and the ambient air will drop. When the differential falls below 90 psi, pilot valve 70 closes and unloader 79 again permits the intake valve of cylinder 11C to function normally, and thereby deliver compressed air to cylinder 11C.

The present invention further comprises heat exchanger 76 connected by conduit reciprocating piston device 10 and receiver tank 14. Compressed air exits reciprocating piston device 10 and enters conduit 84 at a temperature of 250° to 325° F. Heat exchanger 76 lowers the air temperature to within 10–15 degrees of ambient air temperature.

The present invention further comprises air filter 72 connected by 84 between conduit reciprocating piston device 10 and receiver tank 14. The air filter removes water vapor from the compressed air before the air is received by receiver tank 14. The efficiency of air filter 72 is greatly improved by the temperature reduction of the compressed air as provided by heat exchanger 76, enabling the removal of approximately 80 percent of the water vapor entrained in the compressed air.

Such compressed air filters have traditionally been mounted on the outlet side of a compressed air receiver, resulting in large quantities of water in the receiver. The positioning of filter 72 on the inlet side of receiver reduces the quantity of water vapor within tank 14 and lessens the likelihood and frequency of rust, scale, and malfunctions in system control components such as pilot valve 70, air solenoid valves S3 and S4 and exhaust valve unloader 79.

An automatic condensate drain mechanism is also provided with the air receiving subsystem of the present invention. Drain valve 74 is activated by pilot valve 70 every time pilot valve 70 releases a pulse of compressed air to terminate a compression cycle. Thus, every compression cycle is accompanied by an air receiver drain cycle. When drain valve 74 is activated by pilot valve 70, condensate from air receiver tank 14 will be drained through conduit 86 and expelled out waste discharge port 2. Condensate collected in air filter 72 is automatically discharged via a standard float drain (not shown) through conduit 85 and out discharge port 2. Should drain valve 74 or pilot valve 70 malfunction and prevent auto draining, tank 14 could be drained manually through valve 75 in conduit 96, and conduit 85.

A final compressed air coalescing filter (not shown) is attached to air discharge port 1. A high quality filter is used to eliminate 99 percent of oil and bacteria carryover in the processed air stream. Pressurized air delivered from air receiver tank 14 is passed through reheater 80 that accepts heat from heat exchanger 76 to raise the temperature of the air to a level 50–75 degrees above ambient. This enhances condensation of fluid in the final air filter and enables a highly efficient drying process. Thus, the combination of reheater 80 with an air coalescing filter effectively eliminates the need for an expensive refrigerated air drier, such as is normally required in dental applications.

Figure 2:
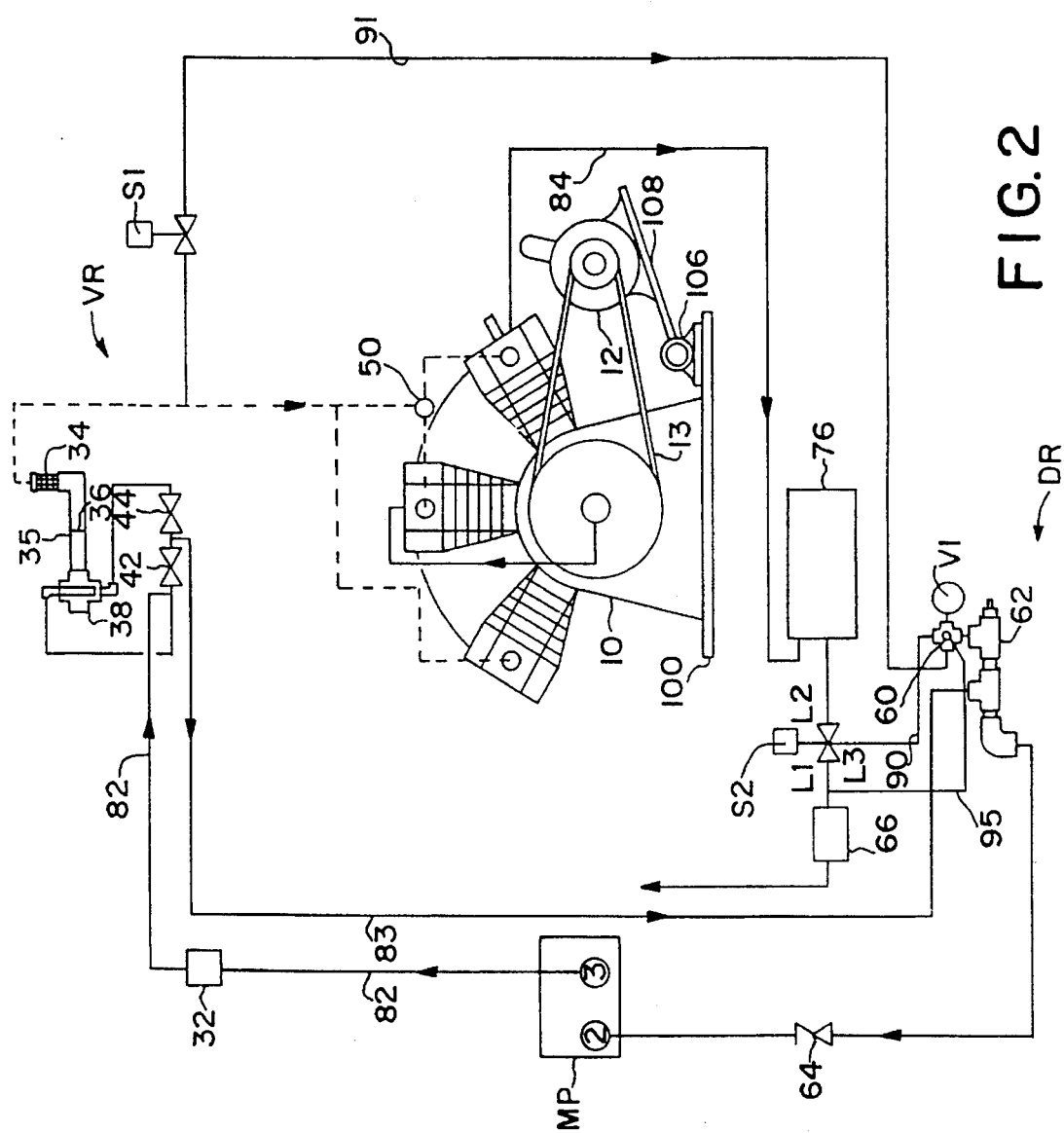
FIG. 2 is a flow diagram of an alternate embodiment of the present invention.

An alternate embodiment of the present invention that provides only vacuum utilities is illustrated in FIG. 2. This embodiment is similar to the vacuum and compressed air supplying apparatus described above, except that the inlet valves of each of the three cylinders are manifolded together to supply a vacuum source. As there is no receiving tank for supplying compressed air, condensate drain cycles are initiated by the pressure of the air exiting the exhaust valves of reciprocating piston device 10.

As before, when the quantity of fluid collected in the DR via conduit 83 reaches a predetermined level, float switch 62 will initiate a drain cycle. Float switch 62 will close, signalling an off-delay timer to energize electrical solenoid drain valves S1 and S2. Solenoid valve S1 closes, divorcing the DR from the VR and its vacuum pressure. Solenoid valve S2 closes leg L1 and opens leg L3 enabling the compressed air escaping a manifold tying together the spring-loaded exhaust valves of reciprocating piston device 10 via conduit 84 to enter conduit 90, pressurizing the DR.

The exhaust valves of reciprocating piston device 10 are designed to be forced open during the compression stroke when the cylinder pressure exceeds the pressure in conduit 84 by approximately one inch of mercury. As the DR is pressurized by slightly compressed air via conduits 84 and 90, check valves 42 and 44 are sealed and fluids in the DR are pushed towards check valve 64. As the pressure in the DR exceeds the 0.5 psi spring pressure of check valve 64, fluids are expelled through discharge port 1. Because a drainage cycle is forced at such a low pressure, the entire apparatus including reciprocating piston device 10 and motor 12 may be installed in a lower level such as a building basement, where the apparatus can expel fluids from the DR to an upper level drain or receiver. Thus, the apparatus can function anywhere that a suitable voltage source is available.

The set point of the off-delay timer connected to float switch 62 determines the duration of the exhaust air charge, usually three to five seconds. When the off-delay timer times out, solenoid valve S2 closes leg 3 and returns exhaust flow to leg 1, and solenoid valve S1 opens to reestablish the pressure link between the DR to the VR. The DR then returns to vacuum pressure and condensate fluids are again permitted to migrate from the VR to the DR. The time span for the entire drain cycle is two to four seconds.

Compressed air exiting the manifolded exhaust valves of reciprocating piston device 10 is routed through heat exchanger 76, three-way solenoid valve S2, and muffler 66 before being vented to the atmosphere. Heat exchanger 76 is provided to protect valve S2 from heat damage.

From the foregoing, it will be seen that this invention is well adapted to attain all ends and objects set forth herein, together with other advantages that are obvious and inherent to the invention.

It will be understood that certain features and subcombinations are of utility and may be employed without reference to other features and subcombinations. This is contemplated by and is within the scope of the claims.

As many possible embodiments may be made of the invention without departing from the scope thereof, it is to be understood that all matter set forth herein or shown in the accompanying figures is to be interpreted as being illustrative and not in a limiting sense.

For example, while this invention is particularly adapted for dental and medical applications, it may be appreciated by one skilled in the art that the vacuum capabilities could be applied in other unrelated areas such as the exploration and production of natural gas from an underground reservoir.

Similarly, this invention could be provided in the form of a two-cylinder reciprocating piston apparatus having first and second cylinders providing vacuum in an intake line, while the first cylinder also provided compressed air in an exhaust line.

What is claimed is:

1. An apparatus for supplying vacuum and compressed air utilities for dental and medical applications, comprising:

a reciprocating piston device having at least two cylinders, one of the cylinders creating a vacuum in an intake line and another of the cylinders producing compressed air in an exhaust line, the vacuum being used to cause air at a pressure below atmospheric to flow through the intake line carrying with it water vapor and effluent from a patient;

means carried by said device for separating the effluent and water vapor from the air in the intake line before the air reaches said device;

means carried by said device for regulating the pressure level of the air in the intake line below atmospheric pressure;

means communicating with said separating means for draining the effluent and water vapor separated from the air in the intake line; and means for receiving the compressed air from said device.

2. The apparatus of claim 1 wherein said device comprises three cylinders, two of said cylinders being manifolded together and connected to the intake line for producing vacuum therein and a third of said cylinders being connected to an exhaust line for producing compressed air therein.

3. The apparatus of claim 1 wherein said separating means comprises a strainer, demister, and drain valve.

4. The apparatus of claim 1 wherein said regulating means comprises a vacuum breaker.

5. The apparatus of claim 1 wherein said draining means comprises a drain conduit, check valve, and float switch.

6. The apparatus of claim 1 wherein said receiving means comprises a receiver conduit, pilot valve, and receiver tank.

7. The apparatus of claim 6 further comprising a heat exchanger connected by said receiver conduit between said device and said receiver tank.

8. The apparatus of claim 6 further comprising an air filter connected by said receiver conduit between said device and said receiver tank for removing water vapor from the compressed air produced by said device before the compressed air is received by said receiver tank.

9. An apparatus for supplying vacuum utilities for dental and medical applications, comprising:

a reciprocating piston device for producing a vacuum to draw air, water vapor, and effluent from a patient toward said device through an intake line connected to said device;

means carried by said device for separating the effluent and water vapor from the air in the intake line before the air reaches said device;

means carried by said device for regulating the pressure level of the air in the intake line below atmospheric pressure; and means communicating with said separating means for collecting and automatically draining the effluent and water vapor separated from the air in the intake line.

10. The apparatus of claim 9 further including:

an electric motor for driving said device;

a drive belt for transferring the torque of said electric motor to said device; and means for pivotally mounting said electric motor to said device and automatically maintaining the tension in said drive belt.

11. The apparatus of claim 9 wherein the crankcase of said device is adapted for carrying all accessory components used with said device.

12. A method of supplying vacuum and compressed air utilities for dental and medical applications, comprising the steps of:

drawing an air stream including water vapor and effluent from a patient through an intake line using the vacuum produced at an intake valve of a reciprocating piston device;

separating and draining the effluent and water vapor from the air stream before the air stream reaches the device; and collecting compressed air from an exhaust valve of the device in a receiver tank.

13. The method of claim 12 further comprising the step of regulating the vacuum of the air stream.

14. A method of supplying vacuum utilities for dental and medical applications, comprising the steps of:

drawing an air stream including water vapor and effluent from a patient through an intake line using the vacuum produced at the intake valve of a reciprocating piston device;

separating and collecting the effluent and water vapor from the air stream before the air stream reaches the device; and draining the collected effluent and water vapor using an indicator that automatically activates a draining sequence to prevent flooding of the device.

* * * * *